United States Patent
Young et al.

[11] Patent Number: 5,417,207
[45] Date of Patent: May 23, 1995

[54] APPARATUS FOR THE INVASIVE USE OF OXIMETER PROBES

[75] Inventors: Robert L. Young, Waukesha; Stephen H. Gorski, Eagle, both of Wis.

[73] Assignee: Sensor Devices, Inc., Waukesha, Wis.

[21] Appl. No.: 163,052

[22] Filed: Dec. 6, 1993

[51] Int. Cl.6 .............................................. A61B 5/00
[52] U.S. Cl. .................................... 128/634; 128/665; 128/736
[58] Field of Search .............................. 128/632–634, 128/637, 664–667, 736; 356/39–41

[56] References Cited

U.S. PATENT DOCUMENTS

| | | |
|---|---|---|
| 4,830,014 | 5/1989 | Goodman et al. |
| 5,007,704 | 4/1991 | McCartney ..................... 128/634 X |
| 5,109,849 | 5/1992 | Goodman et al. .................. 128/633 |
| 5,205,281 | 4/1993 | Buchanan ....................... 128/633 X |
| 5,217,012 | 6/1993 | Young et al. |
| 5,228,440 | 7/1993 | Chung et al. ....................... 128/633 |
| 5,282,464 | 2/1994 | Brain ............................... 128/634 X |
| 5,329,922 | 7/1994 | Atlee, III ......................... 128/634 X |

Primary Examiner—Angela D. Sykes
Attorney, Agent, or Firm—Snell & Wilmer

[57] ABSTRACT

A reflectance oximeter probe is suitably disposed at a distal end of an elongated, substantially flat, semi-rigid chassis configured for insertion into an anatomical canal, for example in the esophagus, rectum or vaginal cavity of a human patient. The reflectance probe may also be suitably employed in many veterinary applications. An electrical connector extends from a proximal end of the chassis and terminates at a plug configured for mechanical and electrical connection to a pulse oximeter box. The reflectance probe includes first and second LED's mounted to an emitter assembly and a detector assembly spaced apart from and mounted substantially coplanar with respect to the emitter assembly. The reflectance probe generates and transmits signals to the oximeter box, the signals indicative of the dynamic oxygen saturation level of the blood perfused mucus membrane tissue.

23 Claims, 3 Drawing Sheets

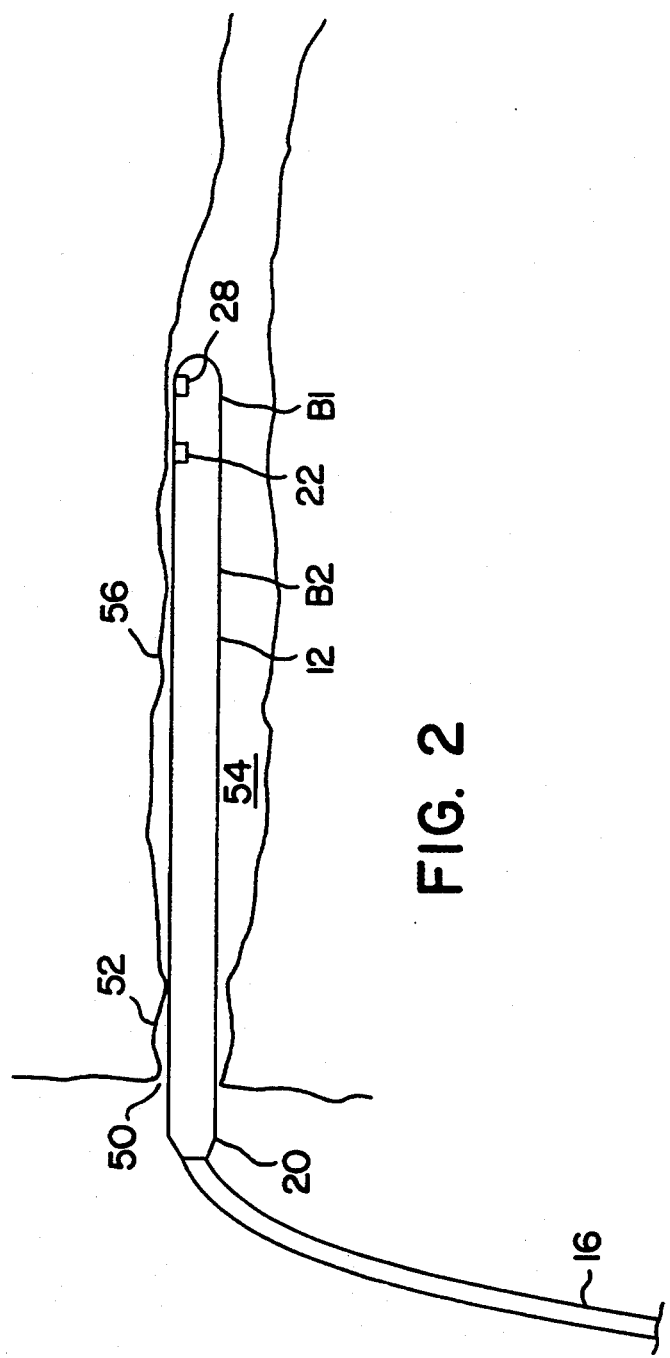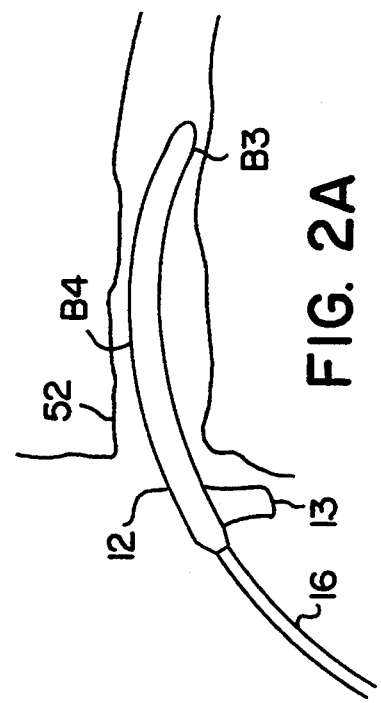

APPARATUS FOR THE INVASIVE USE OF OXIMETER PROBES

TECHNICAL FIELD

The present invention relates, generally, to reflectance pulse oximetry, and more particularly to the invasive, in vivo use of oximeter probes in the esophageal and rectal canals of humans and animals.

BACKGROUND OF THE INVENTION

Pulse oximetry, involving the continuous, non-invasive monitoring of oxygen saturation level in blood perfused tissue, is becoming an increasingly important mechanism for determining patient condition both during and following medical procedures. Indeed, the use of pulse oximeters has expanded in recent years to the point where they are now considered essential in the context of many surgical, emergency room, intensive care, and neonatal applications. The use of pulse oximetry is also expanding into the areas of out-patient surgery centers, oral maxillofacial surgery, home care, and in the veterinary environment.

Pulse oximetry typically involves the use of an oximeter probe (sensor) in contact with the patient. The sensor provides an electrical output signal to an oximeter box, which houses electronic circuitry used to process the electrical signal and generate human-readable indicia of various physiological parameters, including the patient's blood oxygen saturation level and pulse rate. Pulse oximetry systems are currently available from a number of manufacturers, including model no. N-200 manufactured by Nellcor of Chula Vista, Calif.

Non-invasive pulse oximeter probes have traditionally employed transmittance technology, whereby light is passed through a portion of the patient's blood perfused tissue and analyzed to determine the blood saturation level of the tissue. More particularly, traditional oximeter probes comprise an LED assembly and a photodetector assembly spaced apart from each other and mounted to a flexible substrate. This substrate is configured to be attached to a convex portion of the patient's anatomy, for example a finger, toe, ear, and in the case of neonatal applications, to the ball of the foot. The oximeter probe may be conveniently attached to the patient by adhesive, a spring clip, Velcro, and the like. See, for example Young, et al., U.S. Pat. No. 5,217,012 issued Jun. 8, 1993.

When properly attached to a patient, a transmittance oximeter probe is configured such that light emitted by the LED assembly passes through the patient's blood perfused tissue and is received by the photosensor assembly. The absorption characteristics of the transilluminated tissue are related to the oxygen saturation level of hemoglobin flowing through the tissue. Changes in the hemoglobin absorption characteristics influence the amount of light received by the photosensor, thus permitting the direct, non-invasive monitoring of arterial oxygen content. The photosensor assembly produces an output signal indicative of blood oxygen saturation level.

More recently, reflectance technology has been employed in the context of oximeter probes. Reflectance technology involves the use of an emitter assembly and a detector assembly mounted on a substrate and attached to the patient in an essentially co-planar fashion, for example on a patient's forehead or chest. When so mounted, light emitted by the emitter assembly passes through the patient's epidermis and is variously scattered and absorbed by the capillary and arterial beds, sweat glands, sebaceous glands, hair follicles, and the like beneath the patient's skin. During steady state operation of a reflectance probe, changes in the blood oxygen level of the blood perfused tissue proximate the sensor influence the amount of light received by the photosensor assembly in a manner analogous to transmission probes.

The theory of pulse oximetry, whether employed in the context of reflection or transmission sensing devices, states that the light received by the photosensor assembly and, hence, the blood oxygen level of the associated tissue, is a function of, inter alia, the relatively constant absorption characteristics of tissue, venus blood, and the like, as well as the variable absorption characteristics resulting from pulsations in arterial blood flow. Stated another way, the signal emitted by the photosensor assembly includes a DC component which is substantially independent of changes in blood oxygen saturation level, as well as a pulsatile AC component reflective of changes in blood oxygen saturation level.

In order to properly interpret changes in the oxygen saturation level of blood perfused tissue, a reasonably stable arterial pulsation is desired; indeed, an optical differencing measurement is typically made in accordance with this pulsation to determine the patient's pulse rate and oxygen saturation level. Moreover, a certain minimum threshold level of perfusion is generally needed in order to accurately detect changes in blood oxygen saturation level.

While suitable perfusion often exists at extremity sites (e.g., fingers, toes), a number of circumstances inhibit proper perfusion. For example, even in healthy pediatric and neonatal patients, lower mean arterial pressure and smaller arterial pathways inherently restrict the level of perfusion available for interrogation, particularly at the extremities. Moreover, in adults, conditions of critical illness, lowered body temperature, shock, trauma, burn, and other circumstances limit perfusion level as well as the ability to properly interface a sensor to a particular anatomical site. Accordingly, in many risk groups, conventional pulse oximeters are poorly adapted to situations wherein they are most needed. Moreover, many environmental factors, including the effects of changes in ambient light, humidity, and patient movement limit the practical utility of conventional oximeter sensors.

There thus exists a need for an alternate site and monitoring configuration that positively addresses the limitations of presently known sensors.

SUMMARY OF THE INVENTION

An invasive electro-optical sensor probe according to the present invention addresses many of the shortcomings of the prior art.

In accordance with one aspect of the present invention, a reflectance oximeter probe is suitably disposed at a distal end of an elongated, flexible chassis. The chassis is suitably configured for insertion into an anatomical canal, for example in the esophagus, rectum, or vaginal cavity of a human patient. Inasmuch as the hemoglobin oxygen transport mechanism is substantially identical for all mammals as well as many other animals, the reflectance probe in accordance with the present invention, may also be suitably employed in the context of many veterinary applications. This is particularly advantageous inasmuch as many animals are poorly suited for conventional transmittance and reflectance probes due to the presence of hair, fur, and other complications associated with skin thickness, pigmentation, and the like.

In accordance with a further aspect of the present invention, the emitter assembly and detector assembly may be optimally configured for use in the context of an anatomical cavity, for example proximate a mucus membrane, thereby reducing many complications associated with externally attached probes, for example, complications due to ambient light, patient movement, pigmentation, undesirable reflectance due to epidermal skin layers, and the like. Inasmuch as esophageal and rectal sensing sites are typically rich arterial bed sites and, hence, good locations for core oxygen saturation measurements, a greater spacing between the emitter and detector assemblies may be employed and/or a lower signal source may be applied to the emitter assembly while still achieving satisfactory and even superior quality output signals from the detector assembly.

In accordance with a further aspect of the present invention, the reflectance oximeter sensor may be used in conjunction with existing invasive medical apparatus, for example in the context of an endotracheal tube or a core body temperature probe; in such context, the emitter and detector assemblies may be suitably "piggybacked" onto or integrated with the endotracheal, temperature probe, and other such assemblies.

BRIEF DESCRIPTION OF THE DRAWING FIGURES

The present invention will be hereinafter described in conjunction with the appended drawing figures, wherein like designations denote like elements, and:

FIG. 2 shows an exemplary probe inserted into an anatomical canal;

FIG. 2A shows an alternate configuration of the sensor of FIG. 2; and

DETAILED DESCRIPTION OF THE PREFERRED EXEMPLARY EMBODIMENTS

Figure 1:
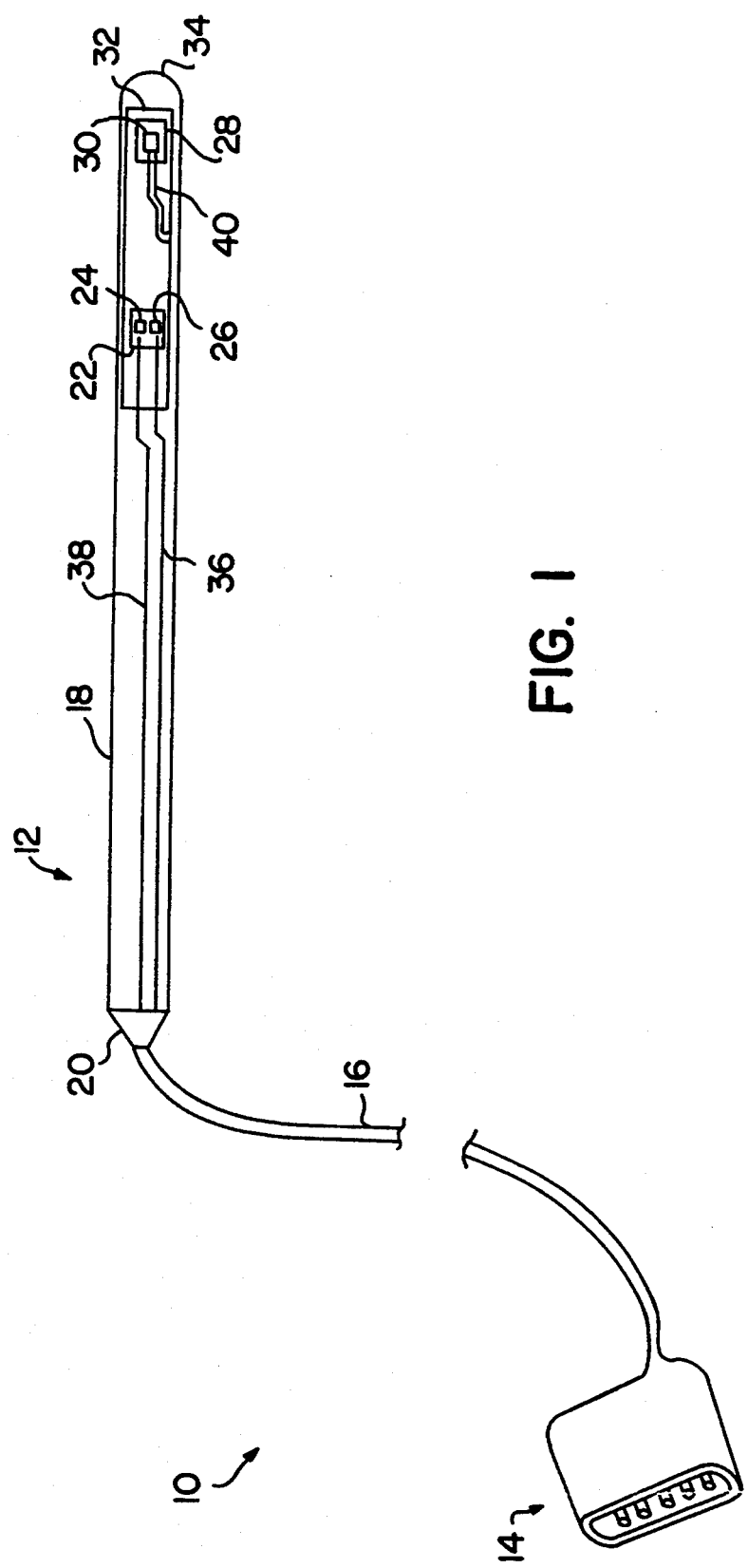
FIG. 1 is a top view of a reflectance probe in accordance with the present invention.

Referring now to FIG. 1, an exemplary probe assembly 10 suitably comprises a chassis 12, a plug 14, and an electrical cable 16 connecting chassis 12 with plug 14. Plug 14 is illustratively configured for mechanical and electrical attachment to an oximeter box or other output assembly configured to display indicia of, inter alia, blood oxygen saturation level, pulse rate, and the like.

In accordance with a preferred embodiment of the present invention, chassis 12 is suitably configured to be removably inserted into an anatomical canal, for example, the esophagus or rectum of a human or animal. Accordingly, cable 16 may be advantageously attached to chassis 12 via a junction 20 which securely grasps cable 16. Moreover, in accordance with a particularly preferred exemplary embodiment, junction 20 and chassis 12 are advantageously of integral, unitary construction to ensure that the device may be completely removed, intact, from an anatomical canal.

In accordance with a further aspect of the present invention, chassis 12 is suitably made from any desired biocompatible material, for example, polyurethane, polyethylene, PVC, PTFE, and the like. In accordance with a further aspect of the present invention, chassis 12 may be rigid, semi-rigid, flexible, or any desired degree of resiliency, depending on the particular application. For example, if the device is configured for use within the rectum of a large animal, e.g., a horse, a higher degree of rigidity may be appropriate. On the other hand, if the device is to be used in the esophagus or trachea in a child or an infant, a high degree of flexibility may be appropriate. Moreover, chassis 12 may comprise any suitable shape in cross-section, depending on, inter alia, the geometry of the anatomical canal within which the device is inserted, the geometry and topology of the optics associated with the device, and the use of the device in conjunction with other medical apparatuses, as discussed in greater detail below. In this regard, chassis 12 may be suitably circular, elliptical, semispherical, arcuate, or substantially flat in cross-section, as desired.

With continued reference to FIG. 1, sensor 10 further comprises an emitter assembly 22 and a detector assembly 28 mounted on the surface of or within chassis 12.

More particularly, emitter assembly 22 suitably comprises one or more light-emitting diodes (LEDs); in the illustrated embodiment, emitter assembly 22 comprises a first LED 24 having a wire 38 connected thereto, and a second LED 26 having a wire 36 connected thereto. Further, said LEDS are electrically connected in parallel such that electrical current flowing in one direction through wires 36 and 38 will cause the first LED 24 to operate, and electric current flowing in the opposite directory will cause the first LED 24 to cease operation and cause the second LED 26 to operate. Respective wires 36, 38 extend along the length of chassis 12, through junction 20, and into cable 16.

Detector assembly 28 suitably comprises a detector 30 configured to sense at least a portion of the output of emitter 22. In the illustrated embodiment, detector 30 comprises a photodetector, for example, a photodiode. A suitable pair of wires 40 interconnects detector 30 and plug 14 via cable 16.

With continued reference to FIG. 1, emitter assembly 22 and detector assembly 28 are suitably mounted to a spacer 32 to thereby maintain a constant spacing between the emitter and detector assemblies.

Emitter assembly 22 and detector assembly 28 are suitably mounted on the surface of or within chassis 12 in a manner which permits light emitted by the emitter assembly to pass through the blood perfused tissue interrogated by sensor 10 and to be received by detector assembly 28. If the emitter and detector assemblies are to be mounted within chassis 12, at least the distal portion of chassis 12 proximate the emitter and detector assemblies advantageously comprises a transmissive material to permit light to pass therethrough in the vicinity of emitter 22 and detector 28. Alternatively, emitter assembly 22 and detector assembly 28 may be mounted on the surface of or integral with the outer wall of chassis 12. In accordance with an alternate embodiment of the present invention, the emitter and detector may suitably be mounted within or otherwise integral with various other medical apparatus, for example, a temperature probe, an endotracheal tube, catheter, and the like.

For veterinary applications, and particularly for esophageal and rectal applications involving large animals, chassis 12 may suitably be in the range of 2 to 24 inches long, and preferably in the range to 4 to 12 inches long, and most preferably 5 to 10 inches long. Chassis 12 may also suitably exhibit a cross-sectional dimension in the range of 0.25 to 1.5 inches and most preferably in the range of 0.3 to 0.8 inches. For applications involving smaller animals, chassis 12 may be on the order of 2 to 12 inches in length, and most preferably in the range of 4 to 5 inches with a cross-sectional dimension in the range of 0.25 to 0.75 inches and most preferably in the range 0.3 to 0.5 inches In this regard, chassis 12 may exhibit any suitable cross-section geometry, e.g., flat, circular, and the like, as discussed above. Moreover, in both veterinary and human applications, chassis 12 may comprise any suitable longitudinal shape, whether straight, curved, angled, arced, and the like, to permit optimal placement of the optical components of the device.

In accordance with a preferred embodiment of device 10 wherein chassis 12 is configured for insertion into a human rectum, chassis 12 is suitably in the range of 3 to 10 inches long, and preferably in the range of 4 to 8 inches long, and most preferably in the range of 5 to 7 inches long. For such rectal applications, chassis 12 may suitably exhibit a circular or elliptical cross-sectional geometry, having a cross-sectional dimension in the range of 0.3 to 1.0 inches, and most preferably in the range of 0.4 to 0.7 inches. For applications involving children and infants, chassis 12 is suitably 3 to 7 inches long, and preferably 4 to 6 inches long, exhibiting a cross-sectional dimension on the order of 0.25 to 0.5 inches, and most preferably 0.35 inches.

In an alternate preferred embodiment, chassis 12 may be configured for insertion into a human esophagus. In this embodiment, chassis 12 suitably is 6 to 16 inches long, and preferably 8 to 14 inches long, and most preferably 9 to 12 inches long. For esophageal applications, although chassis 12 may exhibit any suitable cross-sectional geometry, the present inventors have determined that a substantially flat, elliptical, or arcuate (concave) cross-sectional geometry may facilitate positioning the optical elements within the esophageal canal.

Referring now to FIG. 2, chassis 12 is suitably configured for insertion into an anatomical canal 50, for example, the esophagus or a rectum of a human or animal. More particularly, canal 50 suitably comprises an opening 52, which may comprise a sphincter, a canal passageway 54, and a canal wall 56. In accordance with one aspect of the present invention, chassis 12 is desirably configured such that emitter assembly 22 and detector assembly 28 may be positioned proximate wall 56, suitably in intimate contact therewith.

In accordance with a further aspect of the invention, chassis 12 is suitably configured such that it may be inserted within canal 50 to any desired length, such that junction 20 remains outside the canal. In this regard, it may be desirable to equip chassis 12 with wings (not shown) or other structure in the vicinity of junction 20 to prevent the device from being inserted within the canal beyond junction 20.

Figure 3:
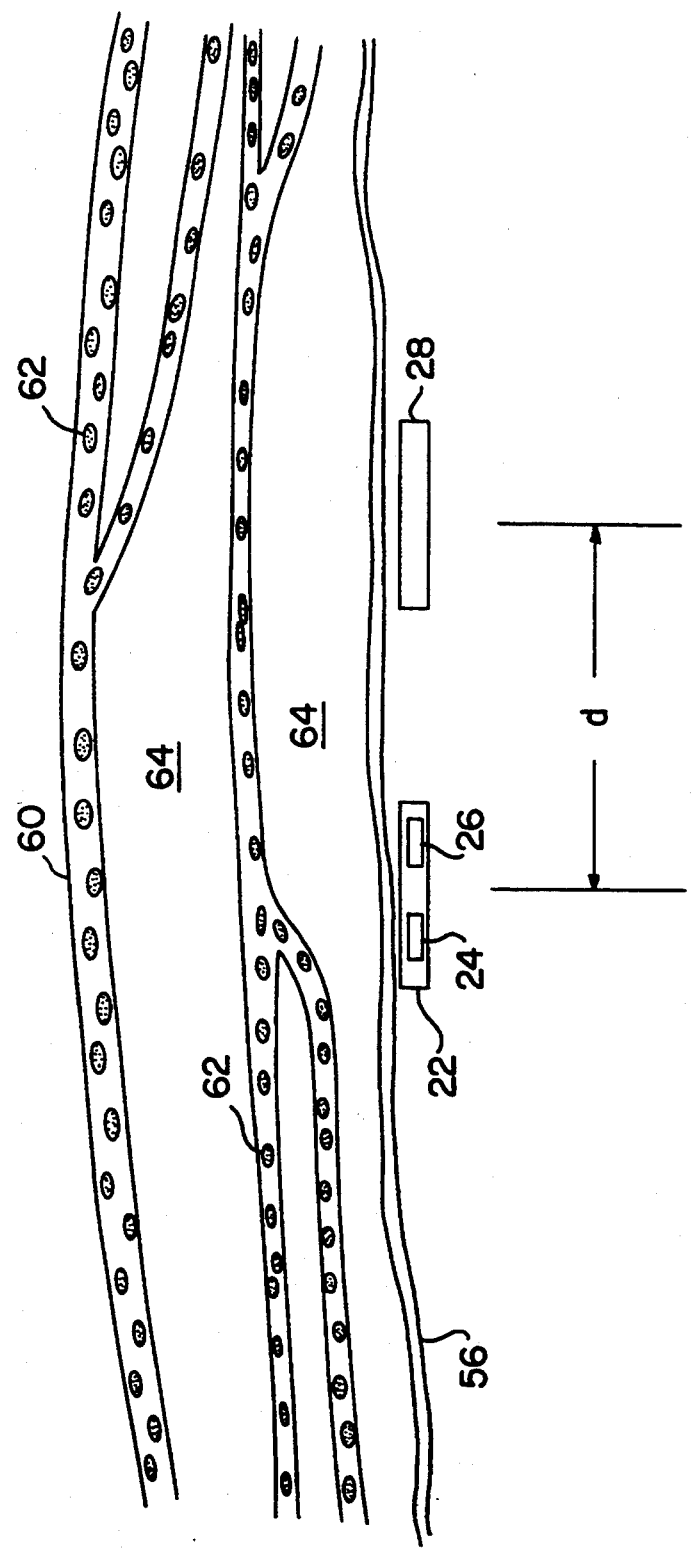
FIG. 3 is a schematic representation of an emitter and detector assembly disposed in situ, and showing the subdermal arterial hemoglobin transport mechanism for a typical patient.

Referring now to FIG. 3, canal wall 56 suitably comprises a mucus membrane, with dermal and subdermal tissue 64 laying beneath the surface of wall 56. An arterial bed comprising various arteries 60 suitably extends throughout the subdermal region proximate wall 56. The arterial blood carried by arteries 60 includes, among other things, blood cells (not shown) and particulate hemoglobin 62.

Pulse oximeters employ the principal of differential light absorption to determine the level of oxygen saturation of hemoglobin in arterial blood. In particular, the light absorption characteristics of oxyhemoglobin are very different from the light absorption characteristics of deoxyhemoglobin. Furthermore, the extinction coefficient for a hemoglobin solution is related to the absorption coefficient of the hemoglobin divided by the concentration. The absorption coefficient of a blood sample, which can be determined based on its oxygenation level and the extinction coefficients associated with the various components of the blood sample, is dependent upon both the wavelength of light used to interrogate the blood sample, as well as the oxygen saturation level of the blood sample.

With continued reference to FIG. 3, light emitted by emitter assembly 22, which is suitably proximate to or in intimate contact with wall 56, passes through tissue 64, arteries 60, and hemoglobin 62. In so doing, a portion of the light is absorbed by these constituents, and some of the light is scattered by these same constituents. The amount of scattered light which is received by detector assembly 28 is a function of, inter alia, the spacing D between emitter 22 and receptor 28, the size and configuration of emitter 22 and detector 28, and the oxygen saturation level of hemoglobin 62 with the arterial bed proximate the probe. By monitoring a characteristic of the output of detector circuit 28 (e.g., voltage, typically current), the oxygen saturation level of the blood perfused tissue may be dynamically and continuously ascertained.

In accordance with a particularly preferred embodiment, two wavelengths of light, for example red and infra red, are desirably emitted by first LED 24 and second LED 26, respectively. As stated above, the light absorption characteristics of oxygenated hemoglobin differ markedly from the absorption characteristics of deoxygenated hemoglobin; at the same time, the difference in absorption characteristics of oxygenated and deoxygenated hemoglobin is also a function of wavelength. In accordance with a preferred embodiment of the invention, the light emitted from emitter 22 is suitably chopped, such that emitter 24 is turned on for a predetermined period, then turned off for a predetermined period to allow the electronics to settle; thereafter, emitter 26 is energized for a predetermined period and thereafter turned off for a predetermined period, and the cycle is repeated. In this way, detector 28 ultimately receives a portion of light emitted at the first wavelength, and thereafter receives a portion of the light emitted at the second wavelength, in a repetitive fashion. As is known in the art, by monitoring two different wavelengths of light, the system can compensate for fluctuations in the level of light received by detector 28 which are unrelated to the level of oxygen saturation of the underlying hemoglobin. See, for example, *Pulse Oximeters,* 185–189 *Health Devices,* Vol. 18, No. 6, (June, 1989); Cui and Ostrander "In Vivo Reflectance On Blood And Tissue As A Function Of Light Wavelength", 630–639 *IEEE Transactions On Biomedical Engineering,* Vol. 37, No. 6 (June, 1990); and Decker, Dickensheets, Arnold, Cheung and Strohl, "A Comparison Of New Reflectance Oximeter With the Hewlett-Packard Oximeter", 122–126, *Biomedical Instrumentation And Technology,* (March/April, 1990).

In accordance with one aspect of the present invention, chassis 12 may be configured for insertion into an anatomical canal, for example the esophagus or rectum of an animal or human. It is notable that many such cavities comprise a mucus membrane wall, a rich arterial bed site. Moreover, by employing a mucus membrane or similar anatomical sight for interrogation, many of the problems associated with non-invasive sensing are eliminated or reduced. For example, light reflectance from the surface of the epidermis is substantially eliminated at a mucus membrane site. In addition, various effects of external light are eliminated, inasmuch as internal anatomical cavities are typically devoid of ambient light. In addition, internal body cavities are often free of hair, fur, fingernails, toenails, cartilage, scar tissue, and many other factors which influence the ability to efficiently pass light through an arterial bed.

In accordance with a further aspect of the invention, it may be possible to manipulate chassis 12 to thereby optimally position the optics with respect to the cavity wall. For example, chassis 12 may be rotated about its longitudinal axis until a robust, stable output is achieved. In addition, it may be desirable to incorporate a balloon, analogous to balloons employed in balloon angioplasty, into chassis 12. More particularly and with momentary reference to FIG. 2, a small balloon may be placed at any point along chassis 12, for example at one of respective points B1 or B2 on the opposite side of chassis 12 from the optical components. Upon inserting chassis 12 into the anatomical cavity, the balloons may be inflated slightly to thereby bias emitter 22 and detector 28 against the cavity wall.

In accordance with an alternate embodiment of the present invention, chassis 12 may suitably be substantially flat or, alternatively, have a first cross-sectional dimension which is significantly greater than a second transverse cross-sectional dimension (e.g., an ellipsoid), such that chassis 12 is substantially self-aligning within a bodily cavity. In this regard, it may also be desirable to place a first emitter assembly and a first detector assembly on one side of the chassis, and a second emitter assembly and a second detector assembly on the opposing side of the distal end of the same chassis, such that light is emitted in opposite directions, i.e., against two opposing walls of the cavity. In accordance with such an embodiment, the output signals from the first and second detector assemblies may be monitored such that the system selects the most desirable signal for display based on, inter alia, signal-to-noise ratio, signal strength, signal stability, and the like.

The foregoing embodiment employing redundant optical circuitry may be particularly advantageous in situations where the anatomical canal may be partially obstructed. For example, in a veterinary application involving horses, often a portion of the rectal canal may be obstructed by fecal matter. When chassis 12 is inserted into the rectal canal, it may become lodged between a canal wall (mucus membrane) and the fecal matter. By monitoring the signal derived from the cavity wall and comparing it to the signal derived from the electronics proximate the fecal matter, it may be possible to utilize the signal from the optoelectronics proximate the cavity wall and disregard the signal from the optics proximate the fecal matter.

In accordance with a further embodiment wherein chassis 12 may be employed in the birth canal of a human or animal (e.g., by inserting the device through the vagina), it may be particularly desirable to employ redundant electronics to sense one or both of the oxygen saturation level of the mother, as well as that of the baby in the birth canal.

In accordance with a further aspect of the invention, chassis 12 may assume any desired shape to permit optimal placement of the electronics proximate the internal cavity wall. For example chassis 12 may suitably be of any desired shape, for example, "banana" shaped; such a configuration would tend to bias the optoelectronics against the cavity wall, for example, by disposing the optoelectronics at point B3 or B4 of chassis 12 (see FIG. 2A). With continued reference to FIG. 2A, it may also be desirable to incorporate a suitable selectively controllable spring mechanism into chassis 12, such that the arc may be increased or decreased in situ, as desired, to achieve optimal placement of the optoelectronics with respect to the cavity wall.

In accordance with yet a further aspect of the present invention, the oximetry optoelectronics may be suitably incorporated into other medical apparatus, including an endotracheal tube, temperature probe, and the like. For those situations in which invasive treatment is required, i.e., the use of an endotracheal tube or a core body temperature probe, pulse oximetry data may be obtained in accordance with the present invention without the need to insert additional invasive apparatus into the patent.

In accordance with yet a further aspect of the invention, a suitable handle 13 or other manual or visual indicia (See FIG. 2A) may be incorporated into the proximal end of chassis 12. Handle 13 permits the physician to dynamically control the degree of axial insertion of the device as well as the rotational position of the device to ensure optimal placement of the optoelectronics. In this regard, handle 13 may be any desired distance from the optoelectronics. By monitoring the position of handle 13 with respect to opening 52 of the anatomical cavity, the precise position of the optoelectronics within the cavity may be unambiguously inferred.

In accordance with yet a further aspect of the invention, various biocompatible lubricants may be employed in conjunction with device 12 to facilitate insertion and removal of the device. Since these lubricants are generally optically transparent at wavelengths of interest and present a DC or steady state attenuation of light only, they generally do not interfere with accurate oxygen readings. Moreover, for those embodiments wherein a controllable spring mechanism is used to control the arc associated with chassis 12 (FIG. 2A), or in those embodiments in which a balloon is employed to position the optoelectronics, these features may also be employed to ensure that chassis 12 remains in place for extended periods of time.

In accordance with a further aspect of the invention, any convenient wavelength or pair of wavelengths may be employed in conjunction with emitter circuit 22. In accordance with a particularly preferred embodiment, first LED 24 suitably emits light in the range of 540 to 690 nanometers, and preferably in the range of 650 to 670 nanometers, and most preferably 660 plus or minus 5 nanometers. Second LED 26 suitably emits light in the range of 880 to 940 nanometers, and preferably in the range of 890 to 920 nanomoters, and most preferably 905 plus or minus 10 nanometers.

In accordance with a further aspect of the invention, the distance D (FIG. 3) between the emitter and the detector assembly is suitably in the range of 0.5 to 5 centimeters, and preferably in the range of 1.5 to 2 centimeters. In certain high sensitivity applications, it may be desirable to slidably mount one or both of the emitter and detector assemblies to permit controlled variation of Distance D during use. In this regard, both the signal strength applied to the emitter circuit and the distance D may be manipulated to achieve optimum data performance.

It will be understand that the foregoing description is of preferred exemplary embodiments of the invention, and that the invention is not limited to the specific forms shown. Various modifications may be made in the design and arrangement of the elements set forth herein without departing from the scope of the invention as expressed in the appended claims.

We claim:

1. An apparatus for invasively monitoring the oxygen saturation level of blood perfused mucus membrane tissue comprising:

an elongated, substantially flat, semi-rigid chassis having a proximal and a distal end;

an electrical connector extending from said proximal end of said chassis and terminating at a plug configured for mechanical and electrical connection to a pulse oximeter box;

respective first and second reflectance optics assemblies disposed on oppositely facing sides of said distal end of said chassis, each of said reflectance optics assemblies comprising:

respective first and second LEDs mounted to an emitter assembly and configured to emit light from said chassis at predetermined respective wavelengths; and a detector assembly, spaced apart from and mounted substantially coplanar with respect to said emitter assembly, and configured to receive at least a portion of the light emitted by said emitter assembly after at least some of said light has passed through said blood perfused mucus membrane tissue;

said reflectance optics assemblies being configured to generate and transmit electrical signals to said oximeter box, said signals being indicative of the dynamic oxygen saturation level of said blood perfused mucus membrane tissue; and a comparator circuit configured to select one of a first electrical signal generated by said first optics assembly, and a second electric signal generated by said second optics assembly, and to facilitate the display of indicia of said selected electrical signal by the oximeter box.

2. The apparatus of claim 1, wherein said chassis has a length in the range of five to ten inches.

3. The apparatus of claim 1, wherein said chassis is substantially elliptical in cross-section.

4. The apparatus of claim 1, wherein said chassis is substantially arcuate in cross-section.

5. The apparatus of claim 1, wherein said chassis exhibits a cross-sectional dimension in the range of 0.25 to 0.75 inches.

6. The apparatus of claim 1, wherein said chassis exhibits a cross-sectional dimension in the range of 0.3 to 0.5 inches.

7. The apparatus of claim 1, wherein said chassis exhibits a substantially arcuate shape along its length.

8. The apparatus of claim 7, wherein said chassis exhibits a banana shape along its length.

9. The apparatus of claim 1, wherein said chassis further comprises means for biasing said first reflectance optics assembly against said mucus membrane tissue.

10. The apparatus of claim 9, wherein said biasing means comprises a spring mechanism configured to urge said first reflectance optics assembly against said mucus membrane tissue.

11. The apparatus of claim 10, wherein said biasing means includes means for selectively controlling said spring mechanism to thereby control the placement of said first reflectance optics assembly along the length of said chassis.

12. The apparatus of claim 1, wherein said chassis comprises an endotracheal tube.

13. The apparatus of claim 12, further comprising a temperature probe proximate a surface of said endotracheal tube.

14. The apparatus of claim 1, wherein said chassis further comprises a temperature probe associated therewith.

15. The apparatus of claim 1, further comprising visual position indicia disposed on said proximal end of said chassis.

16. The apparatus of claim 15, wherein said visual position indicia comprises manual position indicia.

17. The apparatus of claim 1, further comprising means for manually controlling the axial position of said chassis within an anatomical canal.

18. The apparatus of claim 1, further comprising means for manually controlling the rotational position of said chassis within an anatomical canal.

19. The apparatus of claim 1, further comprising an inflatable balloon connected to said chassis for securing said chassis within an anatomical canal.

20. The apparatus of claim 1, wherein said first LED of said first reflectance optics assembly is configured to emit light in the range of 540 to 690 nanometers.

21. The apparatus of claim 1, wherein said second LED of said first reflectance optics assembly is configured to emit light in the range of 880 to 940 nanometers.

22. The apparatus of claim 1, wherein said first LED of said first reflectance optics assembly is disposed in the range of 1.25 to 2.0 centimeters from said detector assembly of said first reflectance optics assembly.

23. The apparatus of claim 1, wherein said first LED of said first reflectance optics assembly is slidably mounted with respect to said detector assembly of said first reflectance optics assembly.

* * * * *